United States Patent [19]
Du et al.

[11] Patent Number: 5,869,965
[45] Date of Patent: Feb. 9, 1999

[54] CORRECTION OF ARTIFACTS CAUSED BY MAXWELL TERMS IN MR ECHO-PLANAR IMAGES

[75] Inventors: Yiping Du; Xiaohong Zhou, both of Pewaukee; Matthew A. Bernstein, Waukesha; Joseph K. Maier, Milwaukee, all of Wis.

[73] Assignee: General Electric Company, Waukesha, Wis.

[21] Appl. No.: 835,669

[22] Filed: Apr. 10, 1997

Related U.S. Application Data

[60] Provisional application No. 60/087,845 Feb. 7, 1997.

[51] Int. Cl.[6] ....................................................... G01V 3/00
[52] U.S. Cl. ............................................. 324/309; 324/307
[58] Field of Search .................................. 324/300, 307, 324/309, 312; 600/410

[56] References Cited

U.S. PATENT DOCUMENTS

| 4,876,509 | 10/1989 | Perlmutter | 324/309 |
| 5,351,006 | 9/1994 | Sumanaweera et al. | 324/309 |
| 5,642,047 | 6/1997 | Bernstein | 324/306 |

FOREIGN PATENT DOCUMENTS

| 4416363 | 11/1995 | Germany . |

OTHER PUBLICATIONS

Lai, "Reconstructing NMR images under magnetic fields with large inhomogeneities" J. Phys. E: Sci. Instrum., vol. 15, pp. 1093–1100, 1982.

Weis et al., "Simulation of the Influence of Magnetic Field Inhomogeneity and Distortion Correction in MR Imaging" Magnetic Resonance Imaging vol. 8, pp. 483–489, 1990.

*Primary Examiner*—Louis Arana
*Attorney, Agent, or Firm*—Quarles & Brady

[57] ABSTRACT

A method for correcting Maxwell field induced distortion, ghosting, and blurring artifacts in non-axially oriented EPI images is disclosed. In one embodiment phase corrections are calculated and used to offset Maxwell term errors during the image reconstruction process, and in another embodiment corrections are made after the image is reconstructed.

10 Claims, 4 Drawing Sheets

CORRECTION OF ARTIFACTS CAUSED BY MAXWELL TERMS IN MR ECHO-PLANAR IMAGES

CROSS REFERENCE TO RELATED APPLICATION

This application is based on provisional application Ser. No. 60/087,845, filed on Feb. 7, 1997 and entitled "CORRECTION OF ARTIFACTS CAUSED BY MAXWELL TERMS IN EPI MR IMAGES".

BACKGROUND OF THE INVENTION

The field of the invention is nuclear magnetic resonance imaging methods and systems. More particularly, the invention relates to the correction of image artifacts caused by "Maxwell terms" produced by MRI systems.

When a substance such as human tissue is subjected to a uniform magnetic field (polarizing field $B_0$), the individual magnetic moments of the spins in the tissue attempt to align with this polarizing field, but precess about it at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins, and after the excitation signal $B_1$ is terminated, this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

It is well known that imperfections in the linear magnetic field gradients ($G_x$, $G_y$, and $G_z$) produce artifacts in the reconstructed images. It is a well known problem, for example, that eddy currents produced by gradient pulses will distort the gradient fields and produce image artifacts. Methods for compensating for such eddy current errors are also well known as disclosed, for example, in U.S. Pat. Nos. 4,698,591; 4,950,994; and 5,226,418.

It is also well known that the gradients may not be perfectly uniform over the entire imaging volume, which may lead to image distortion. Methods for compensating this non-uniformity are described, for example, in U.S. Pat. No. 4,591,789.

Other than uncompensated eddy current errors and gradient non-uniformity errors that escape correction, it can be assumed that the magnetic field gradients ($G_x$, $G_y$, and $G_z$) produce linear magnetic fields exactly as programmed, thus spatially encoding the NMR data accurately. With these gradients, the overall static magnetic field at location (x,y,z) is conventionally given as $B_0 + G_x x + G_y y + G_z z$, and the direction of the field is usually thought to be along the z-axis. This description, however, is not exactly correct. As long as a linear magnetic field gradient is applied, the overall magnetic field is nutated away from the z-axis and its amplitude exhibits higher-order spatial dependencies ($x^2$, $y^2$, $z^2$, $z^3$, ...). These phenomena are a direct consequence of the Maxwell equations which require that the overall magnetic field satisfy the following two condition: $\nabla \cdot B = 0$ and $\nabla \times B = 0$. The higher-order magnetic fields, referred to as "Maxwell terms" (or Maxwell fields), represent a fundamental physics effect, and are not related to eddy currents or imperfection in hardware design and manufacture. Although Maxwell terms have been known for at least a decade, their effect on imaging has been largely ignored because of their minute consequences for conventional imaging conditions.

Echo-planar imaging ("EPI") is one of the ultrafast MR imaging techniques that has many clinical applications. Consider, for example, a superconducting MRI system where the main magnetic field is oriented along the long axis of the patient. EPI can then suffer from severe image distortion when the imaged slice is oriented in a sagittal or coronal plane and frequency or phase encoding is performed along the direction of the polarizing magnetic field $B_0$. In addition, there is a certain amount of ghosting and blurring in such images. The image distortion, ghosting, and blurring in such images are caused by the Maxwell terms. As a result, EPI has been usually limited in both clinical and research applications to axially oriented slices which are perpendicular to the magnetic field $B_0$.

SUMMARY OF THE INVENTION

The present invention is a method for reducing or eliminating Maxwell-induced image artifacts in EPI images that are acquired with a non-axial slice orientation. More specifically, the method includes: a) acquiring a k-space data set using an EPI pulse sequence; b) calculating a Maxwell-term induced phase error for signals emanating from locations at a distance (z) from the system isocenter; c) applying a phase correction to the k-space data set; d) reconstructing an image from the k-space data set; e) saving the data in the reconstructed image corresponding to locations at distance (z) from the system isocenter; and repeating steps b) through e) at different distances (z) until image data for a complete image throughout the desired region of interest are saved.

A general object of the invention is to eliminate distortion, ghosting and blurring produced by Maxwell terms in non-axial EPI images. By making an image distortion correction during the image reconstruction process, all image artifacts can be eliminated.

In another embodiment of the invention phase corrections are made to a non-axial EPI image after image reconstruction. Processing time is much less for this embodiment of the invention, but only the distortion and not the ghosting or blurring artifacts are eliminated by this correction method.

GENERAL DESCRIPTION OF THE INVENTION

Figure 1:
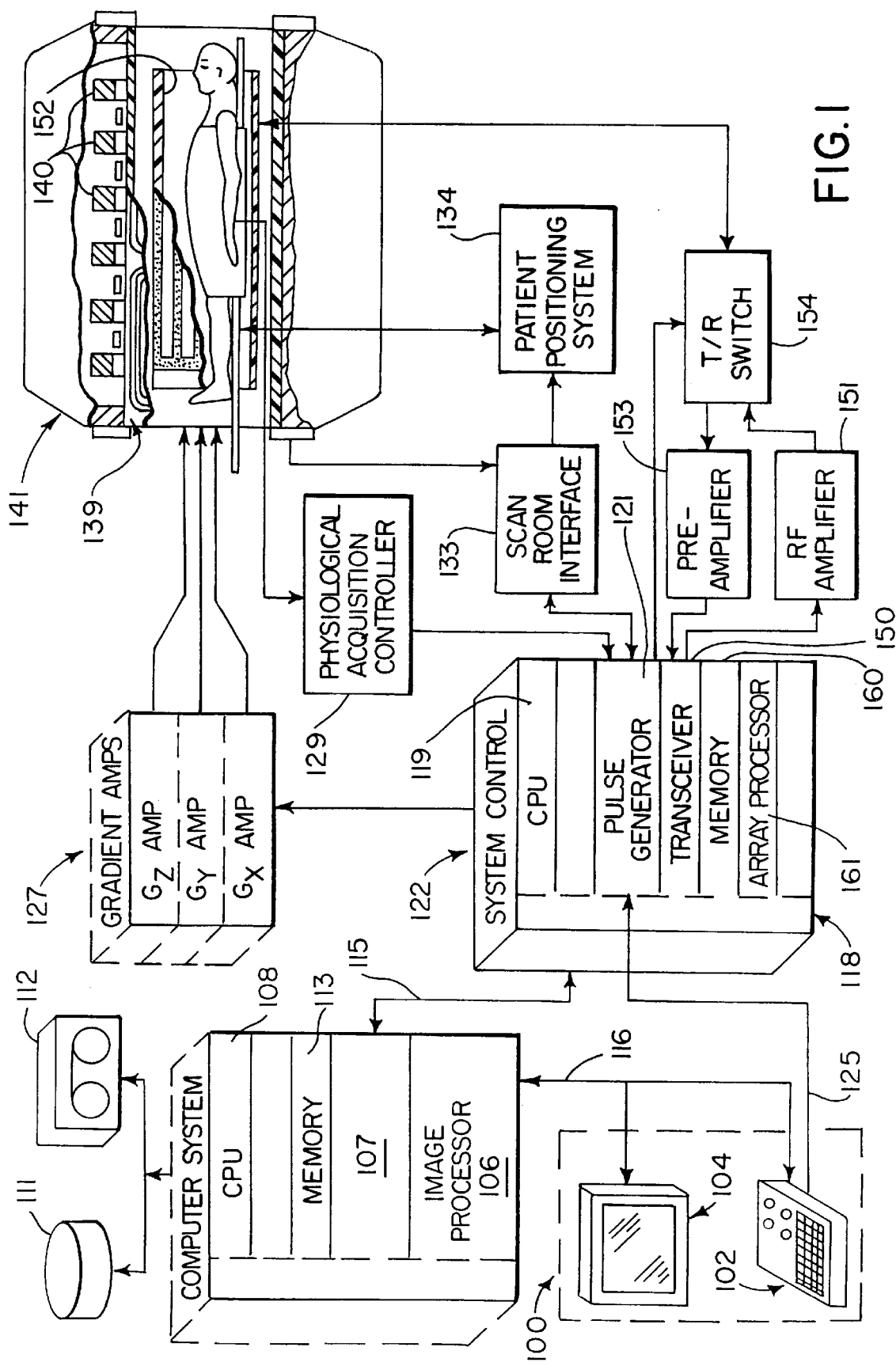
FIG. 1 is a block diagram of an MRI system which employs the present invention.

The Maxwell terms are basically the higher-order spatial gradients (second order, third order, etc.) produced by the linear magnetic field gradients (x, y and z-gradients). These terms can be directly derived from the Maxwell equations. According to the Maxwell equations, a magnetic field B must satisfy the following two conditions:

$$\vec{\nabla} \cdot \vec{B} = 0 \quad \text{(divergence equation),} \tag{1a}$$

$$\vec{\nabla} \cdot \vec{B} = \mu_0 \epsilon_0 \frac{\partial \vec{E}}{\partial t} + \mu_0 \vec{J} \quad \text{(curl equation),} \tag{1b}$$

where $\nabla$ is the derivative operator ($\nabla = \hat{i}\partial/\partial x + \hat{j}\partial/\partial y + \hat{k}\partial/\partial z$), E is the electric field, J is the current density, and $\mu_0$ and $\epsilon_0$ are the magnetic permeability and the electric permeability of the free space, respectively. If there is zero current density and the electric field is static, equation 1b reduces to:

$$\nabla \times B = 0. \tag{1c}$$

From equations 1a and 1c, we obtain:

$$\frac{\partial B_x}{\partial x} + \frac{\partial B_y}{\partial y} + \frac{\partial B_z}{\partial z} = 0, \tag{2}$$

$$\frac{\partial B_x}{\partial y} = \frac{\partial B_y}{\partial x}, \tag{3a}$$

$$\frac{\partial B_y}{\partial z} = \frac{\partial B_z}{\partial y}, \tag{3b}$$

$$\frac{\partial B_z}{\partial x} = \frac{\partial B_x}{\partial z}. \tag{3c}$$

The above 4 equations 2 and 3a–c contain a total of 9 partial derivatives, among which only 5 are independent. Our next task is to select these five independent variables. Recognizing that $$\frac{\partial B_z}{\partial x} \equiv G_x, \frac{\partial B_z}{\partial y} \equiv G_y, \frac{\partial B_z}{\partial z} \equiv G_z$$

($G_x$, $G_y$, and $G_z$ are the linear gradients), we can readily choose $G_x$, $G_y$, and $G_z$ as the first three independent variables. For a radially symmetric $G_z$-field in cylindrical coordinates $\partial B_x/\partial x$ and $\partial B_y/\partial y$ should be identical. However, to cover a more general case, we choose a dimensionless symmetry parameter $\alpha$ as the fourth independent variable:

$$\alpha \equiv -\frac{\partial B_x/\partial x}{G_z}, \text{ or } 1 - \alpha \equiv -\frac{\partial B_y/\partial y}{G_z}. \tag{4a-b}$$

The last independent variable can be conveniently chosen as (based on equation 3a):

$$g \equiv \frac{\partial B_x}{\partial y} = \frac{\partial B_y}{\partial x}. \tag{5}$$

At this point, all the partial derivatives described in equations 2 and 3 can be expressed using the 5 independent variables $G_x$, $G_y$, $G_z$, $\alpha$ and g:

$$\begin{bmatrix} \frac{\partial B_x}{\partial x} & \frac{\partial B_x}{\partial y} & \frac{\partial B_x}{\partial z} \\ \frac{\partial B_y}{\partial x} & \frac{\partial B_y}{\partial y} & \frac{\partial B_y}{\partial z} \\ \frac{\partial B_z}{\partial x} & \frac{\partial B_z}{\partial y} & \frac{\partial B_z}{\partial z} \end{bmatrix} = \begin{bmatrix} -\alpha G_z & g & G_x \\ g & -(1-\alpha)G_z & G_y \\ G_x & G_y & G_z \end{bmatrix}. \tag{6}$$

With all the terms, the overall magnetic field becomes:

$$B = \hat{i}B_x + \hat{j}B_y + \hat{k}B_z, \tag{7}$$

where, to first order, $$\begin{bmatrix} B_x \\ B_y \\ B_z - B_0 \end{bmatrix} = \begin{bmatrix} \frac{\partial B_x}{\partial x} & \frac{\partial B_x}{\partial y} & \frac{\partial B_x}{\partial z} \\ \frac{\partial B_y}{\partial x} & \frac{\partial B_y}{\partial y} & \frac{\partial B_y}{\partial z} \\ \frac{\partial B_z}{\partial x} & \frac{\partial B_z}{\partial y} & \frac{\partial B_z}{\partial z} \end{bmatrix} \begin{bmatrix} x \\ y \\ z \end{bmatrix} = \tag{8}$$

$$\begin{bmatrix} -\alpha G_z & g & G_x \\ g & -(1-\alpha)G_z & G_y \\ G_x & G_y & G_z \end{bmatrix} \begin{bmatrix} x \\ y \\ z \end{bmatrix}.$$

The above equations have two important implications. First, the $B_0$-field is no longer aligned along the z-axis because of the transverse fields $B_x$ and $B_y$. Second, the amplitude of the main magnetic field is not simply given by $B = B_0 + G_x x + G_y y + G_z z$, but instead by $$B(x,y,z) = \sqrt{B_x^2 + B_y^2 + B_z^2} \tag{9}$$

($B_0 + G_x x + G_y y + G_z z$ merely represents the z-component of the overall field). If we perform three sequential Taylor series expansions on equation 9 with respect to x, y, and z, respectively, it can be seen that the magnetic field not only has its regular zeroth and first order spatial dependencies, but also shows higher-order spatial components. The result of the Taylor expansion to the second order is given by equation 10:

$$B = B_0 + G_x x + G_y y + G_z z + \frac{1}{2B_0}[\alpha^2 G_z^2 + g^2]x^2 + \tag{10}$$

$$\frac{1}{2B_0}[(1-\alpha)^2 G_z^2 + g^2]y^2 + \frac{1}{2B_0}[G_x^2 + G_y^2]z^2 + \frac{gG_z}{B_0}xy +$$

$$\frac{1}{B_0}[gG_x - (1-\alpha)G_y G_z]yz + \frac{1}{B_0}[gG_y - \alpha G_x G_z]xz.$$

For gradient systems used in MRI, we have g=0, and $\alpha \approx \frac{1}{2}$ (due to the cylindrical symmetry). Under these conditions, equation 10 reduces to:

$$B = B_0 + G_x x + G_y y + G_z z + \frac{1}{8B_0} G_z^2 x^2 + \frac{1}{8B_0} G_z^2 y^2 + \tag{11}$$

$$\frac{1}{2B_0}[G_x^2 + G_y^2]z^2 - \frac{1}{2B_0} G_y G_z yz - \frac{1}{2B_0} G_x G_z xz.$$

Equations 10 and 11 indicate that, whenever a linear magnetic field gradient is applied, higher-order gradient fields will be produced to satisfy the Maxwell equations. These higher-order gradient fields are referred to as the "Maxwell terms", or "Maxwell fields."

With the inclusion of the Maxwell terms, the 2D NMR signal equation becomes:

$$S(k_x, k_y) = \int_x \int_y \rho(x,y) e^{-i(k_x x + k_y y)} e^{-i\phi_M} dx dy, \tag{12a}$$

$$\phi_M = \gamma \int_t B_M(G_x, G_y, G_z, x, y, z) dt', \tag{12b}$$

-continued
$$B_M = \frac{1}{8B_0} G_z^2 x^2 + \frac{1}{8B_0} G_z^2 y^2 + \frac{1}{2B_0} [G_x^2 + G_y^2]z^2 - \frac{1}{2B_0} G_y G_z yz - \frac{1}{2B_0} G_x G_z xz. \quad (12c)$$

where $B_M$ is the Maxwell magnetic field and $\phi_M$ is the associated phase error, which we call the Maxwell phase. As implied by equation 12, the Maxwell phase error depends on the details of each pulse sequence. In some pulse sequences, the phase error can be zero and thus it causes no image degradation. In most other sequences, a non-zero phase error is produced, giving various image quality problems such as distortion, ghosting, image shift, shading, blurring, and intensity variation.

Maxwell field induced EPI image distortion is caused primarily by the Maxwell field generated during the readout of the NMR signals using an alternating readout gradient. This distortion is the same for coronal and sagittal oriented image, if the readout gradient is applied along the z-axis. In the following discussion the correction for coronal images is derived, but the same correction applies to sagittal images by exchanging the x and y coordinates.

According to equation (12c) the Maxwell field is different in the case where the readout, or frequency encoding gradient is along the z-direction from the case where the frequency encoding is along the x-direction (i.e., swap phase-frequency). In a coronal slice with offset $y = y_0$, when the frequency encoding is along the x-direction and the phase encoding is along the z-direction, the Maxwell field is $$B_M = \frac{G_x^2 z^2}{2B_0}. \quad (13)$$

In the same coronal slice, when the frequency encoding is along the z-direction and the phase encoding is along the x-direction, the Maxwell field is:

$$B_M = \frac{G_z^2(x^2 + y_0^2)}{8B_0}. \quad (14)$$

It is noted that the coefficient of the Maxwell field in equation (13) is four times larger than that in equation (14) when $y_0 = 0$. In the following, we only discuss the case where the phase encoding is along the z-direction. In the case where the frequency encoding is along the z-direction, similar equations can be analogously derived using equation (14) instead of equation (13).

Figure 3:
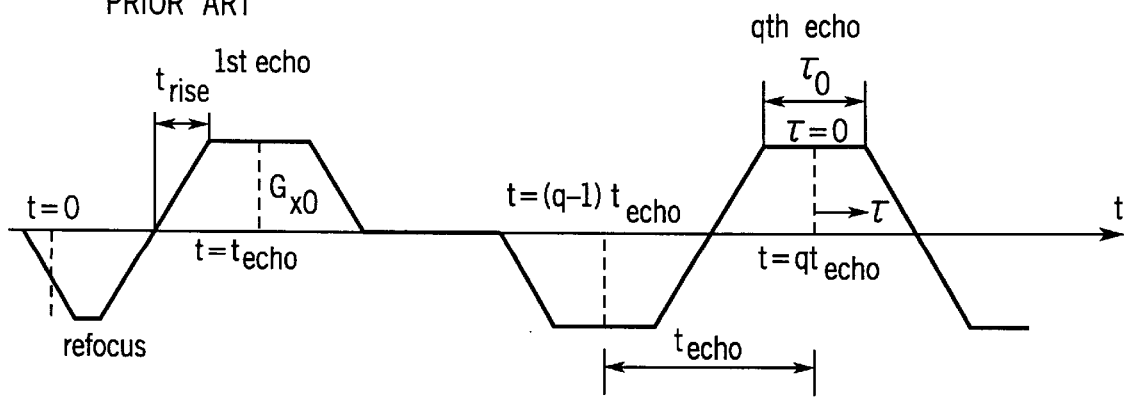
FIG. 3 is a graphic representation of read-out gradient used in an EPI pulse sequence.

In EPI, the k-space data are acquired by a series of bipolar readout gradient lobes as shown in FIG. 3. The Maxwell field generated by this readout gradient creates a time varying phase:

$$\Phi_M = \gamma \int_0^t B_M(z,t) dt \quad (15)$$

$$= \frac{\gamma}{2B_0} \int_0^{qt_{echo} + \tau} G_x^2(t) z^2 dt \quad (16)$$

$$= \frac{\gamma}{2B_0} qz^2 \int_0^{t_{echo}} G_x^2(t) dt + \frac{\gamma}{2B_0} z^2 \int_0^\tau G_{x0}^2 dt \quad (17)$$

$$= \frac{\gamma}{2B_0} G_{x0}^2 \left( t_{echo} - \frac{4}{3} t_{rise} \right) qz^2 + \frac{\gamma}{2B_0} G_{x0}^2 \tau z^2 \quad (18)$$

where $G_{x0}$ is the amplitude of the readout gradient, $t_{echo}$ is the time interval between two consecutive echoes (i.e. echo spacing), $t_{rise}$ is the rise-time of the readout gradient, $\tau$ is a time variable starting from an echo center, and q is echo index (q=1, ..., $N_y$) After flipping every other row of the sampled data in the k-space for image reconstruction, we have:

$$\Phi_M(p,q) = \frac{\gamma}{2B_0} G_{x0}^2 \left( t_{echo} - \frac{4}{3} t_{rise} \right) qz^2 + (-1)^{q-1} \frac{\pi}{B_0} G_{x0} \left( p + \frac{1}{2} \right) \Delta k_x z^2, \quad (19)$$

where the increment of $k_x$ corresponding to sampling interval, $\Delta\tau$, is:

$$\Delta k_x = \frac{\gamma}{2\pi} G_{x0} \Delta\tau = \frac{1}{FOV_x}, \quad (20)$$

where $FOV_x$ is the field of view in the frequency-encoding direction, and the index for each sampled complex point along $k_x$ is $p = -N_x/2, \ldots N_x/2 - 1$. Equation (20) can be modified for ramp sampling.

From equation (19), the Maxwell phase linearly accumulates along the phase-encoding direction for a specific z value (see the first term in equation (19).

According to the Fourier shift theorem:

If $F^{-1}\{G(\omega)\} = g(t)$, then, $F^{-1}\{G(\omega)e^{-i\alpha\omega}\} = g(t-\alpha)$, (21)

where $F^{-1}$ indicates inverse Fourier transform, a linear phase accumulation causes image pixel shift along the phase-encoding direction. Because the amount of pixel shift depends on the |z| value, the Maxwell phase described by the first term in equation (19) causes image distortion in the phase-encoding direction.

It is also apparent from equation (19) that the Maxwell phase linearly accumulates along the readout direction for a specific z value (see the second term in equation (19)). Because of the alternating sign of the second term, the Maxwell phase accumulation does not simply cause an image distortion along the frequency-encoding direction. With an additional linear phase along $k_x$, the image, $\rho'(m,n)$, reconstructed using an inverse Fourier transform is $$\rho'(m,n) = \frac{1}{2} \{\rho(m + \beta_x N_x, n) + \rho(m - \beta_x N_x, n)\} + \frac{1}{2} \left\{ \rho\left(m + \beta_x N_x, n + \frac{N_y}{2}\right) - \rho\left(m - \beta_x N_x, n + \frac{N_y}{2}\right) \right\}, \quad (22)$$

where $\rho(m,n)$ is the object, $N_x$ is the matrix size of the image along the frequency-encoding direction and $\beta_x$ is the slope of the linear phase along the frequency-encoding direction:

$$\beta_x = \frac{1}{2B_0} \Delta k_x G_{x0} z^2 = \frac{1}{2B_0} \frac{G_{x0}}{FOV_x} z^2. \quad (23)$$

Note that $\beta_x$ is proportional to $z^2$.

From equation (22), we see that the first two terms form the image of the object and the last two terms form a Nyquist ghost. The image of the object is the average of two images shifted in opposite directions. The averaging of the two shifted image causes image blurring. The blurring increases as $z^2$ increases because the amount of shift is proportional to $z^2$. From equation (22) we also see that the Nyquist ghost is the difference of the two shifted images with a shift of half FOV in the phase-encoding direction. This indicates that the ghost should be more conspicuous at locations that have large |z| value and are near sharp edges.

Equations (19) and (23) were derived for the coronal images with the phase-encoding direction along the z-direction. Similar equations can be analogously derived for coronal images with the phase encoding along the x-direction and the frequency encoding along the z-axis. In the case where the coronal image has zero offset (i.e. $y_0=0$), the Maxwell field effect is one-quarter of that shown in equation (19) and (23).

Although Equs. (19) and (20) are rigorously valid only for the case where data sampling occurs during a constant readout gradient, the same principle can be generalized for the case where the data sampling occurs with a time-varying readout gradient, for example the ramp sampling. In this case, kx will be determined according to the gradient waveform, sampling interval, and FOV.

The applications of the phase correction method discussed above can also be extended to other MRI pulse sequences where a readout gradient train is used to sample multiple k-space lines for a single image. These MRI pulse sequences include, but are not limited to, Gradient and Spin Echo (GRASE), unipolar EPI (i.e., skip-echo EPI), 3D EPI, and echo-train Fast Gradient Echo (FGRE).

Because the phase error caused by the Maxwell field is known (see equation (19)), image distortion, ghosting, and blurring can be eliminated if a phase correction is made during the image reconstruction. Such a phase correction can be performed by calculating the Maxwell phase and subtracting it from the phase of the acquired k-space data before applying the inverse Fourier transform. This subtraction can be best accomplished by multiplying each complex k-space data point by a complex exponential:

$$k(p,q) = e^{i\phi_M(p,q,|z|)},$$

Because the Maxwell phase is a function of the spatial coordinate $|z|$, however, this phase correction needs to be performed separately for each $|z|$ value. For a coronal image with the phase encoding in the z-direction, the phase correction needs to be repeated $N_z/2$ times, where $N_z$ is the matrix size of the image along the phase-encoding direction, because two rows in the digital image with z and −z spatial coordinates have the same Maxwell phase.

Alternatively, the correction of the Maxwell field effect can be performed after the image is reconstructed. In this "post-reconstruction" correction, only image distortion can be corrected. As discussed above, the Maxwell field causes image pixel shift along the phase-encoding direction. The image distortion generated by the Maxwell field can be corrected by shifting the pixels in the reconstructed image. The amount of the shift is a quadratic function of the axial coordinate, z:

$$\delta z = \frac{\Phi_M(q) - \Phi_M(q-1)}{2\pi} FOV_z = \qquad (24)$$

$$\frac{\gamma}{4\pi B_0} G_{x0}^2 \left( t_{echo} - \frac{4}{3} t_{rise} \right) FOV_z z^2,$$

where δz is the amount of pixel shift, and $FOV_z$ is the field of view along the phase-encoding direction. Note that, in the above discussion, the phase-encoding direction is along the physical z-direction.

In two-dimensional (2D) images, image distortion is associated with the deformation of pixel dimensions and the variation of the pixel area. Because the image intensity is proportional to the pixel area, the variation of pixel area causes a variation of image intensity. Such image intensity variation can also be corrected when the variation of pixel area is known. This post reconstruction correction is analogous to the correction used for gradient non-uniformity as described in U.S. Pat. No. 4,591,789. There, however, gradient non-uniformity and not phase errors from Maxwell terms are being corrected.

Figure 4:
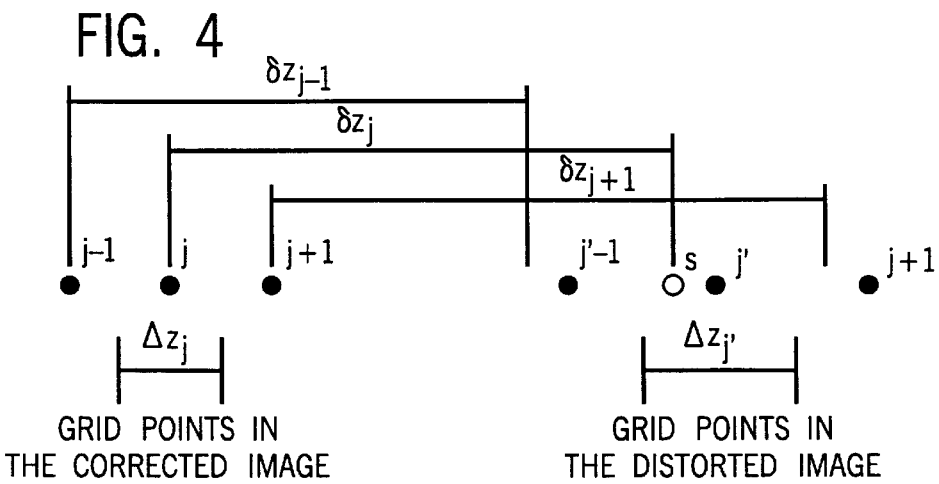
FIG. 4 is a graphic representation of one of the corrective steps employed in the method of the present invention.

According to equation (24), the amount of pixel shift is different for pixels with different $|z|$ values. In FIG. 4, three solid dots on the right side represent three consecutive grid points in the distorted image; three solid dots on the left side represent the corresponding grid points in the corrected image after pixel shifting. From FIG. 4, pixel dimension change after pixel shifting can be calculated using a first order approximation:

$$\Delta z_{j'} = \frac{1}{2}\left[(z_{j+1} + \delta z_{j+1}) - (z_{j-1} + \delta z_{j-1})\right] \qquad (25)$$

$$= \Delta z_j - \frac{1}{2}(\delta z_{j+1} - \delta z_{j-1}).$$

where, $$\Delta z_j = \frac{1}{2}(z_{j+1} - z_{j-1}).$$

Then, the intensity correction factor, $\Omega_j$, for the intensity variation at j is:

$$\Omega_j = \frac{\Delta z_{j'}}{\Delta z_j} = 1 - \frac{(\delta z_{j+1} - \delta z_{j-1})}{(z_{j+1} - z_{j-1})}. \qquad (26)$$

Using equation (16), equation (18) can be rewritten as:

$$\Omega_j = \frac{\Delta z_{j'}}{\Delta z_j} = 1 - Cz. \qquad (27)$$

where C is a constant, $$C = \frac{\gamma}{\pi B_0} G_{x0}^2 \left( t_{echo} - \frac{4}{3} t_{rise} \right) FOV_y. \qquad (28)$$

For a grid point in the corrected image, the corresponding point in the distorted image usually is not located exactly at a grid point. Linear interpolation is used to obtain the intensity value of this corresponding point using the intensities of its two nearest neighboring grid points, although other interpolation algorithms can be used. In FIG. 4, the point in the distorted image corresponding to the grid point j is located between the grid points j'−1 and j', A linear interpolation is applied using the intensities at j'−1 and j'.

In the event that the shift causes a pixel to be moved to a point outside the FOV, this pixel is wrapped around to the other side of the FOV to avoid blank regions in the image.

Note that although this post-reconstruction method for correction is able to correct image distortion, it is not able to correct the ghosting and image blurring generated by the Maxwell field as described in the second term of equation (19).

Both the phase correction method and the post-construction method discussed above can also be extended to the case where the imaging slice is in an oblique direction. The Maxwell phase in an oblique slice can be calculated using Equ. (11) with the rotation matrix of the oblique slice.

DESCRIPTION OF THE PREFERRED EMBODIMENT

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprising of $G_x$, $G_y$, and $G_z$ amplifiers. Each gradient amplifier excites a corresponding gradient coil in an assembly generally designated 139 to produce the magnetic field gradients used for spatially encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 may operate to Fourier transform the data into an image data set. This image data set is conveyed through the serial link 115 to the computer system 107 where it is corrected in accordance with the post-reconstruction method described above and stored in the disk memory 111. In the alternative, the Maxwell term phase error can be subtracted from the raw, k-space data in memory module 160 as will be described in more detail below. The corrected k-space data is then Fourier transformed by the array processor 161 and stored in the disk memory 111. In response to commands received from the operator console 100, this image data may be archived on the tape drive 112, or it may be further processed by the image processor 106 and conveyed to the operator console 100 and presented on the display 104.

Figure 2:
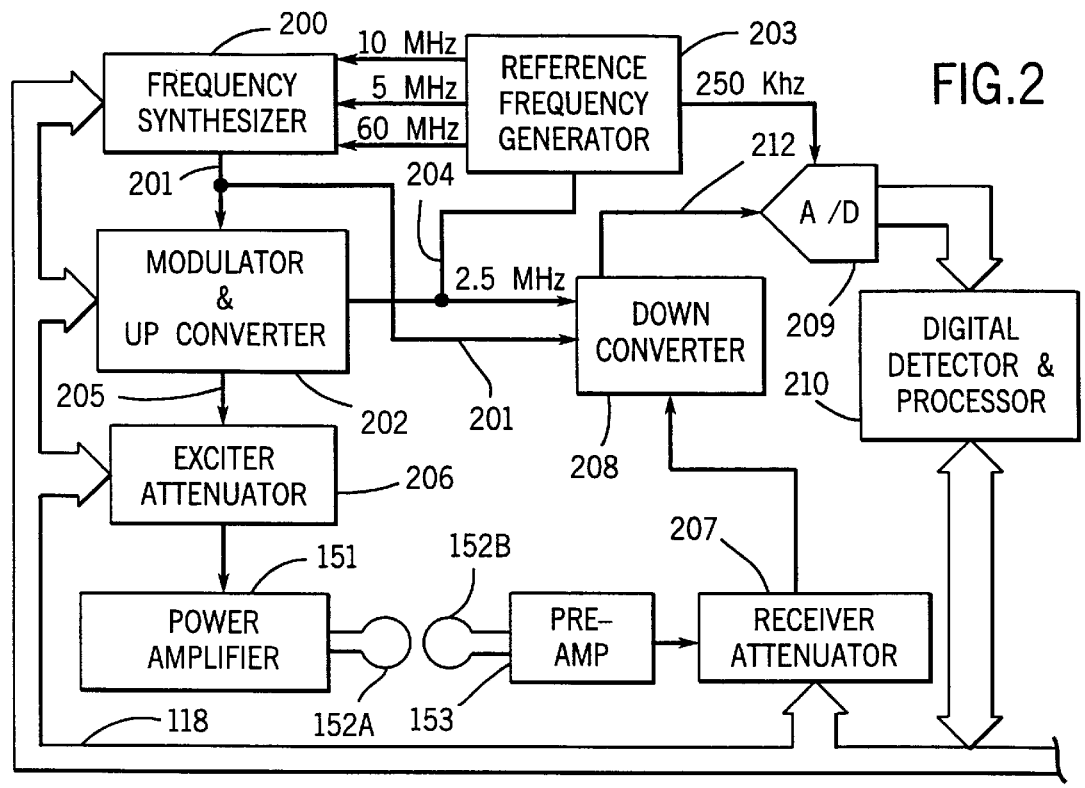
FIG. 2 is an electrical block diagram of the transceiver which forms part of the MRI system of FIG. 1.

Referring particularly to FIGS. 1 and 2, the transceiver 150 produces the RF excitation field B1 through power amplifier 151 at a coil 152A and receives the resulting signal induced in a coil 152B. As indicated above, the coils 152A and B may be separate as shown in FIG. 2, or they may be a single coil as shown in FIG. 1. The base, or carrier, frequency of the RF excitation field is produced under control of a frequency synthesizer 200 which receives a set of digital signals (CF) from the CPU module 119 and pulse generator module 121. These digital signals indicate the frequency and phase of the RF carrier signal produced at an output 201. The commanded RF carrier is applied to a modulator and up converter 202 where its amplitude is modulated in response to a signal R(t) also received from the pulse generator module 121. The signal R(t) defines the envelope of the RF excitation pulse to be produced and is produced in the module 121 by sequentially reading out a series of stored digital values. These stored digital values may, in turn, be changed from the operator console 100 to enable any desired RF pulse envelope to be produced.

The magnitude of the RF excitation pulse produced at output 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIGS. 1 and 2 the signal produced by the subject is picked up by the receiver coil 152B and applied through the preamplifier 153 to the input of a receiver attenuator 207. The receiver attenuator 207 further amplifies the signal by an amount determined by a digital attenuation signal (RA) received from the backplane 118.

The received signal is at or around the Larmor frequency, and this high frequency signal is down converted in a two step process by a down converter 208 which first mixes the NMR signal with the carrier signal on line 201 and then mixes the resulting difference signal with the 2.5 MHz reference signal on line 204. The down converted NMR signal is applied to the input of an analog-to-digital (A/D) converter 209 which samples and digitizes the analog signal and applies it to a digital detector and signal processor 210 which produces 16-bit in-phase (I) values and 16-bit quadrature (Q) values corresponding to the received signal. The resulting stream of digitized I and Q values of the received signal are output through backplane 118 to the memory module 160 where they are employed to reconstruct an image.

The 2.5 MHz reference signal as well as the 250 kHz sampling signal and the 5, 10 and 60 MHz reference signals are produced by a reference frequency generator 203 from a common 20 MHz master clock signal.

Figure 5:
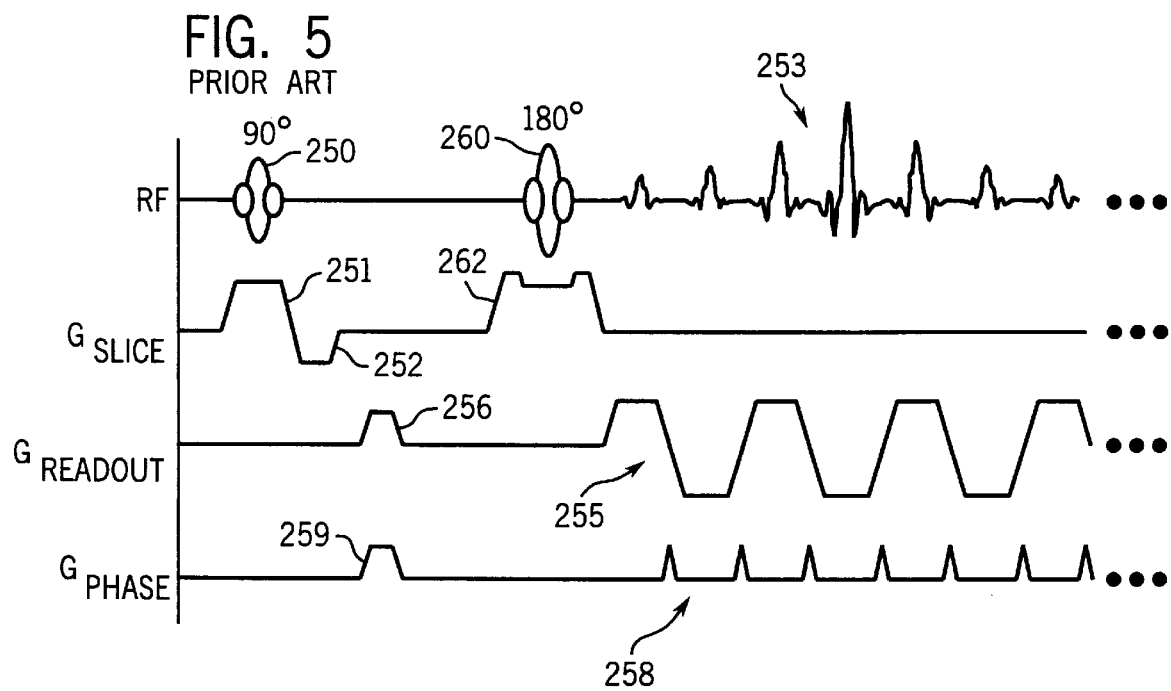
FIG. 5 is a graphic representation of an EPI pulse sequence used to practice the present invention.

The EPI pulse sequence employed in the preferred embodiment of the invention is illustrated in FIG. 5. A 90°

RF excitation pulse 250 is applied in the presence of a slice selection gradient pulse 251 to produce transverse magnetization in a slice. The excited spins are rephased by a negative lobe 252 on the slice selection gradient and then a time interval elapses before a 180° RF refocusing pulse 260 is applied in the presence of a slice-select gradient pulse 262. A number of NMR echoes (e.g., 128), indicated generally at 253 are acquired during the EPI pulse sequence. Each NMR echo signal 253 is a different view which is separately phase encoded to scan $k_y$-space (e.g., from $k_y=-64$ to $k_y=+63$) in monotonic order. The pre-phasing phase-encoding gradient pulse 259 is chosen such that the view acquired at $k_y=0$ occurs at the desired echo time (TE).

The NMR echo signals 253 are gradient recalled echoes produced by the application of an oscillating readout gradient 255. The readout sequence starts with a prephasing readout gradient lobe 256 and the echo signals 253 are produced as the readout gradient oscillates between positive and negative values. A number of samples (e.g., 128) are taken of each NMR echo signal 253 during each readout gradient pulse 255. The successive NMR echo signals 253 are separately phase encoded by a series of phase encoding gradient pulses 258. A prephaser phase encoding lobe 259 occurs before the echo signals are acquired to encode the first view. Subsequent phase encoding pulses 258 occur as the readout gradient pulses 255 switch polarity, and they step the phase encoding monotonically upward through $k_y$-space.

Figure 6:
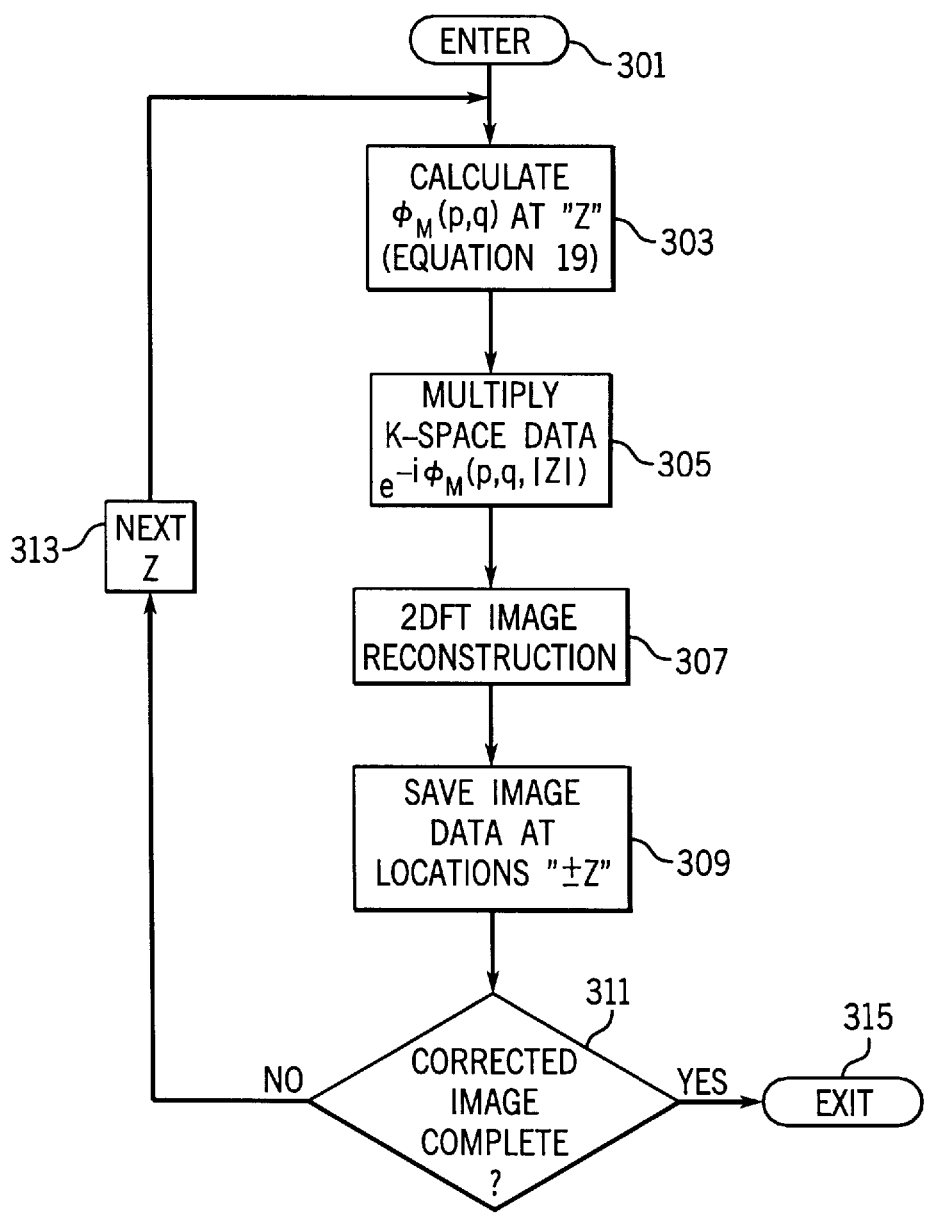
FIG. 6 is a flow chart illustrating the steps performed by the method of the present invention.

A scan is performed using the EPI pulse sequence of FIG. 5 for a coronal image. The readout, phase-encoding and slice selection direction are along the x, y and z-axes, respectively. The raw k-space data are stored in the memory module 160 and are corrected for the Maxwell field phase errors before the 2DFT image reconstruction is performed. The method used to perform the correction is illustrated by the flow chart in FIG. 6 which depicts the steps used by a program. Referring particularly to FIG. 6, a loop is entered at 301 in which two rows of image data at the locations +z and −z in the reconstructed image are corrected. The process remains in this loop until all the rows of image data have been corrected. More specifically, the phase error $\phi_M(p,q)$ is calculated using equation (19) discussed above for a selected ±z location, as indicated by process block 303. The array of phase errors $\phi_M(p,q)$ are then used to correct the phase of the array of raw k-space data as indicated at process block 305. This correction is made by subtracting the phase error from the phase of each corresponding k-space sample point. This phase subtraction can be readily accomplished by multiplying the complex k-space data point by an exponential factor: $e^{-i\Phi_M(p,q)}$.

Then, as indicated at process block 307, a two-dimensional inverse Fourier transform is performed on the corrected k-space data set to produce an image array. However, only the image data in the rows at +z and −z are accurately corrected, and only these image data are saved as indicated at process block 309. A check is made at decision block 311 to determine if all the rows in the image data have been corrected, and if not, the process loops back to correct the next pair of rows at a different +z location as indicated by process block 313. Eventually all of the phase corrected rows of the reconstructed image are produced and the process exits at 315.

For an image with the center of the FOV aligned with z=0, two rows in the distortion-corrected image, that have the same |z| values, can be retained for the final image during each loop through the above process. Using this approach, the 2-D inverse FFT needs to be repeated $N_y/2$ times. The computation time for image reconstruction can be further reduced by using a one-dimensional (1-D) inverse FFT. In this approach, a 1-D inverse FFT is applied to each of the k-space data array columns, a total of $N_x$ times. Then, a 1-D inverse FFT is applied to each of the two rows that have the same |z| values, a total of two times. This process is repeated $N_y/2$ times (i.e. perform a 1-D inverse FFT a total number of $(N_x+2)N_y/2$ times) in order to reconstruct the entire image. The computation time for a 2-D inverse FFT of an array with $N_xN_y$ elements is:

$$T_{2-D}=\lambda N_x N_y \log_2(N_xN_y). \tag{29}$$

The computation time for a 1-D inverse FFT of an array with $N_x$ elements is:

$$T_{1-D}=\lambda N_x \log_2(N_x), \tag{30}$$

where $\lambda$ is a constant determined by the implementation of the inverse FFT algorithm and by the computation power of the computer. Based on equations (29) and (30), the computation time for $(N_x+2)N_y/2$ times of a 1-D inverse FFT is approximately half ($=\frac{1}{2}+1/N_y$, when $N_x=N_y$) of the computation time for $N_y/2$ times of a 2-D inverse FFT. Therefore, for an image with N×N elements, the reconstruction time is increased when this method is used by a factor of N/4 compared to a conventional reconstruction algorithm without the correction for Maxwell field effect, assuming the computation time for phase subtraction prior to the FFT is negligible. Although rarely acquired, for images with off-center FOV, the phase correction must be applied to each of the rows in the asymmetric part of the FOV, and the processing time increases.

It should be apparent that although this preferred Maxwell term correction method corrects for distortion, ghosting and blurring, it requires considerable data processing time to accomplish. This processing can be reduced by employing the post-reconstruction method described above. The post-reconstruction method is performed in the computer system 107 after the image is reconstructed. The post-reconstruction method is implemented in the following steps:

1) Calculate the value of |z| for each pixel in the corrected image, I(i,j), (it is initially blank). Calculate the amount of pixel shift along the phase-encoding direction, $\delta z_j$, using equation (24).

2) Find the corresponding point, s, in the distorted image. Obtain the intensity value of this corresponding point, I'(i,s) (s is no longer an integer), by applying linear interpolation using the image intensities of its two nearest neighbors, I'i(i,j'−1), and I'(i,j').

3) Calculate the intensity correction factor, $\Omega_j$, for this point using equations (27) and (28).

4) Obtain the intensity of the distortion-corrected image using the multiplication of $\Omega_j$ and I'(i,s):I(i,j)=$\Omega_j$I'(i,s).

5) Obtain the distortion corrected image, I(i,j), by repeating Step 1 to 4 for all the pixels. Because all the pixels in a row in the corrected image have the same z value, the computation efficiency of the above method can be further improved by calculating $\delta z_j$ and $\Omega_j$ only once for each row.

We claim:

1. A method for correcting Maxwell term errors produced by an NMR system during the acquisition of an NMR image data array using an echo-planar pulse sequence, the steps comprising:

a) acquiring a k-space data set using the echo-planar pulse sequence;

b) calculating a Maxwell phase error for signals emanating from locations at a distance (|z|) from an NMR system isocenter;

c) applying the Maxwell phase error as a phase correction to the k-space data set;

d) reconstructing an image data set from the phase corrected k-space data set;

e) saving the data in the image data set corresponding to locations at the distance ($|z|$) in the NMR image data array; and f) repeating steps b) through e) at different distances ($|z|$) until the entire image data array is saved.

2. The method as recited in claim 1 in which the calculation of the phase correction in step b) is determined by the parameters of the echo-planar pulse sequence.

3. The method as recited in claim 2 in which the parameters of the pulse sequence include amplitude of its readout gradient ($G_{x0}$), the time interval between the centers of two consecutive NMR echo signals ($t_{echo}$), and the rise time of the readout gradient ($t_{rise}$).

4. The method as recited in claim 3 in which the calculation of the Maxwell phase error is performed using the following formula $$\Phi_M(p,q) = \frac{\gamma}{2B_0} G_{x0}^2 \left( t_{echo} - \frac{4}{3} t_{rise} \right) qz^2 +$$

$$(-1)^{q-1} \frac{\pi}{B_0} G_{x0} \left( p + \frac{1}{2} \right) \Delta k_x z^2,$$

where:

q is the index for the acquired echo signal, p is the index for each sample along the frequency encoding axis, $\gamma$ is the gyromagnetic constant, $B_0$ is the amplitude of the main magnetic field, and $\Delta k_x$ is the sampling interval along the frequency encoding axis.

5. The method as recited in claim 1 in which the image reconstruction in step d) is performed by performing a Fourier transformation along a phase-encoding axis of the k-space data set, followed by a Fourier transformation along a readout axis of the k-space data set at the locations $+z$ and $-z$.

6. A method for correcting Maxwell term errors produced by an NMR system during the acquisition of an NMR image data array using an echo-planar pulse sequence, the steps comprising:

a) acquiring a k-space data set using the echo-planar pulse sequence;

b) reconstructing a distorted image data set from the k-space data set;

c) calculating corrections for distortion along a phase encoding axis due to Maxwell terms using parameters of the echo-planar pulse sequence;

d) correcting the distorted image data set using the calculated corrections by shifting the location of pixels in the image data set along the phase encoding axis; and e) calculating the intensity of pixels in the NMR image data array using values in the distorted image data set from corresponding locations therein.

7. The method as recited in claim 6 in which step d) is performed by interpolating between pixel values in the distorted image data set.

8. The method as recited in claim 6 in which the parameters of the pulse sequence include the amplitude of its readout gradient ($G_{x0}$), the time interval between centers of two consecutive NMR echo signals ($t_{echo}$), and the rise-time of the readout gradient ($t_{rise}$).

9. The method as recited in claim 8 in which the calculation of the correction in step c) is performed using the following formula:

$$\delta z = \frac{\gamma}{4\pi B_0} G_{x0}^2 \left( t_{echo} - \frac{4}{3} t_{rise} \right) FOV_z z^2$$

where:

$\delta_z$ is the corrective shift along the phase encoding axis, $\gamma$ is the gyromagnetic constant, $B_0$ is the amplitude of the main magnetic field, and $FOV_z$ is the field of view of the NMR image along the phase encoding axis z.

10. The method as recited in claim 8 in which the intensity calculated in step d) is performed using the following formula:

$$\Omega_j = 1 - Cz,$$

where C is a constant:

$$C = \frac{\gamma}{\pi B_0} G_{x0}^2 \left( t_{echo} - \frac{4}{3} t_{rise} \right) FOV_z, \text{ and}$$

where $\Omega_j$ is the intensity correction factor at j, $\gamma$ is the gyromagnetic constant $B_0$ is the amplitude of the NMR system magnetic field, and $FOV_z$ is the field of view of the NMR image data array along the frequency encoding axis z.

* * * * *